(12) United States Patent
Lee et al.

(10) Patent No.: US 12,216,837 B2
(45) Date of Patent: Feb. 4, 2025

(54) INPUT DEVICE AND INTERFACE DEVICE INCLUDING THE SAME

(71) Applicant: Samsung Display Co., Ltd., Yongin-si (KR)

(72) Inventors: Taehee Lee, Hwaseong-si (KR); Chul Kim, Hwaseong-si (KR); Hee Seomoon, Seoul (KR); Hyeon Jun Lee, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/219,688

(22) Filed: Mar. 31, 2021

(65) Prior Publication Data
US 2022/0050535 A1    Feb. 17, 2022

(30) Foreign Application Priority Data
Aug. 12, 2020    (KR) .................. 10-2020-0101179

(51) Int. Cl.
| | |
|---|---|
| *G06F 3/01* | (2006.01) |
| *A61B 5/00* | (2006.01) |
| *A61B 5/021* | (2006.01) |
| *A61B 5/024* | (2006.01) |
| *A61B 5/1455* | (2006.01) |
| *G06F 3/0354* | (2013.01) |
| *G06F 3/044* | (2006.01) |

(52) U.S. Cl.
CPC ...... *G06F 3/03545* (2013.01); *A61B 5/02141* (2013.01); *A61B 5/02433* (2013.01); *A61B 5/14552* (2013.01); *A61B 5/6897* (2013.01); *G06F 3/0441* (2019.05); *G06F 3/0442* (2019.05)

(58) Field of Classification Search
CPC .... G06F 3/0442; G06F 3/0446; G06F 3/0441; G06F 3/03545; G06F 2203/04111; G06F 3/01; G06F 3/015
See application file for complete search history.

(56) References Cited

U.S. PATENT DOCUMENTS

| | | | | |
|---|---|---|---|---|
| 4,513,437 | A * | 4/1985 | Chainer ................... | B43K 8/22 |
| | | | | 382/314 |
| 5,774,571 | A * | 6/1998 | Marshall ................... | G07C 9/35 |
| | | | | 382/119 |
| 6,454,482 | B1 * | 9/2002 | Silverbrook ........... | B43K 8/006 |
| | | | | 346/140.1 |
| 6,724,374 | B1 * | 4/2004 | Lapstun ............. | H04N 1/32122 |
| | | | | 345/173 |
| 7,057,608 | B2 * | 6/2006 | Lapstun ............. | H04N 1/00358 |
| | | | | 358/468 |

(Continued)

FOREIGN PATENT DOCUMENTS

| | | | |
|---|---|---|---|
| KR | 10-2017-0067077 | A | 6/2017 |
| KR | 10-2019-0134378 | A | 12/2019 |

*Primary Examiner* — Olga V Merkoulova
(74) *Attorney, Agent, or Firm* — Lewis Roca Rothgerber Christie LLP

(57) ABSTRACT

An input device includes: a housing having a transmissive portion; a communicator in the housing and configured to exchange a signal externally; a pressure sensor in the housing along an inner circumferential surface of the housing; and a measurement sensor in the housing and facing the transmissive portion.

19 Claims, 15 Drawing Sheets

(56) References Cited

U.S. PATENT DOCUMENTS

| | | | |
|---|---|---|---|
| 7,936,482 B2* | 5/2011 | Takezaki | G06F 3/03545 345/173 |
| 9,049,998 B2 | 6/2015 | Brumback et al. | |
| 9,063,588 B2* | 6/2015 | Buelow | G06F 3/03545 |
| 9,575,573 B2* | 2/2017 | Chang | G06F 3/03545 |
| 10,037,093 B2* | 7/2018 | Yamamoto | G06F 3/03545 |
| 10,466,808 B2 | 11/2019 | Yi et al. | |
| 10,517,489 B2 | 12/2019 | Narasimhan et al. | |
| 10,627,923 B2* | 4/2020 | Ruscher | H02J 50/10 |
| 10,702,171 B2 | 7/2020 | Narasimhan et al. | |
| 2002/0025062 A1* | 2/2002 | Black | G07C 9/37 382/116 |
| 2006/0158440 A1* | 7/2006 | Ashenbrenner | G06F 3/016 345/179 |
| 2008/0245583 A1* | 10/2008 | Lapstun | G06F 3/016 178/19.05 |
| 2009/0182240 A1* | 7/2009 | Jang | A61B 5/0245 600/504 |
| 2012/0062521 A1* | 3/2012 | Ahn | G06F 3/04166 345/179 |
| 2014/0002422 A1* | 1/2014 | Stern | G06F 3/0383 345/179 |
| 2014/0035887 A1* | 2/2014 | Kim | G06F 3/03545 345/179 |
| 2014/0267180 A1* | 9/2014 | Buelow | G06F 3/03545 345/179 |
| 2014/0267184 A1* | 9/2014 | Bathiche | G06F 1/3259 345/179 |
| 2015/0346890 A1* | 12/2015 | Zachut | G06F 3/041661 345/174 |
| 2015/0363012 A1* | 12/2015 | Sundara-Rajan | G06F 3/0441 345/179 |
| 2016/0179222 A1* | 6/2016 | Chang | G06F 3/03545 345/179 |
| 2016/0320918 A1* | 11/2016 | Hara | G06F 3/04162 |
| 2017/0068340 A1* | 3/2017 | Zimmerman | G06F 3/0416 |
| 2017/0068345 A1* | 3/2017 | Barel | G06F 3/0441 |
| 2018/0081455 A1* | 3/2018 | Huston | G06F 3/03545 |
| 2019/0187817 A1* | 6/2019 | Zimmerman | G06F 3/03545 |
| 2019/0357779 A1 | 11/2019 | Park et al. | |
| 2019/0384402 A1* | 12/2019 | Huizar | G06F 3/016 |
| 2020/0033947 A1 | 1/2020 | Bloom et al. | |
| 2020/0085323 A1* | 3/2020 | Lee | A61B 5/6843 |
| 2020/0089340 A1* | 3/2020 | Ruscher | G06F 3/0383 |
| 2020/0245878 A1* | 8/2020 | Kang | A61B 5/0261 |
| 2021/0303089 A1* | 9/2021 | Ruscher | G06F 3/044 |

* cited by examiner

FIG. 2A
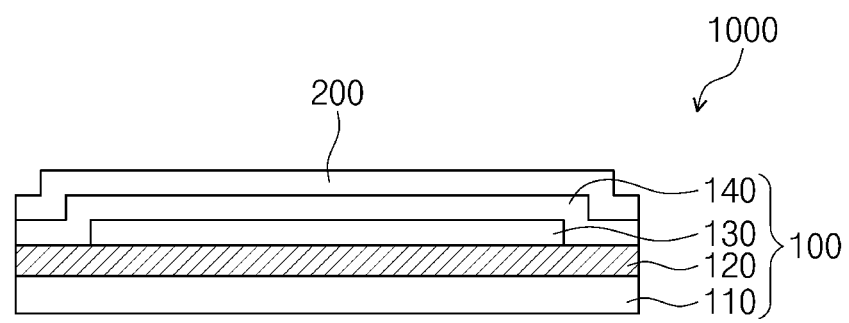
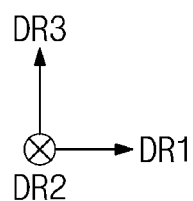
FIG. 2B
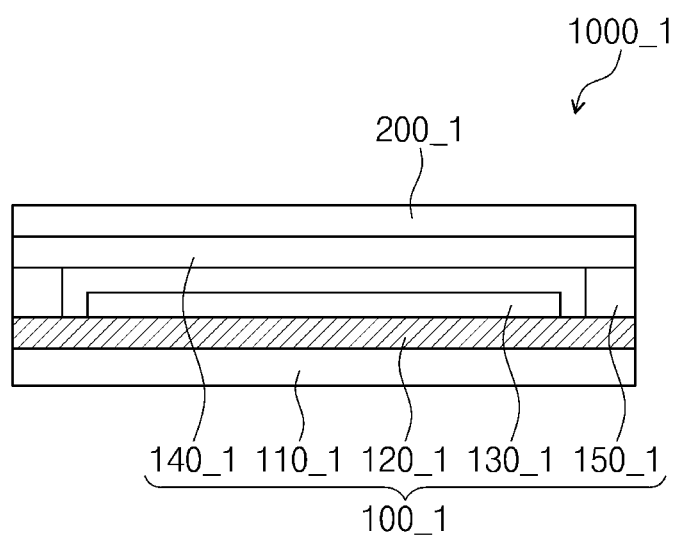

INPUT DEVICE AND INTERFACE DEVICE INCLUDING THE SAME

CROSS-REFERENCE TO RELATED APPLICATION

The present application claims priority to and the benefit of Korean Patent Application No. 10-2020-0101179, filed on Aug. 12, 2020, the entire content of which are hereby incorporated by reference.

BACKGROUND

Aspects of some example embodiments of the present disclosure relate to an input device capable of sensing biometric information and an interface device including the same.

Multimedia electronic devices such as televisions, mobile phones, tablet computers, navigation devices, game machines, and the like are provided with a display device for displaying images. Electronic devices may be provided with not only typical input units such as buttons, keyboards, mice, and the like but also input sensors for providing touch-based input schemes for enabling users to intuitively and conveniently input information or commands with ease.

Input sensors may detect a touch or pressure applied using a body of a user. Furthermore, there is an increasing demand for active pens for detailed touch input for particular application programs (e.g., application programs for sketching or drawings) or users who are familiar with inputting information using writing instruments.

The above information disclosed in this Background section is only for enhancement of understanding of the background and therefore the information discussed in this Background section does not necessarily constitute prior art.

SUMMARY

Aspects of some example embodiments of the present disclosure include an input device capable of sensing biometric information and an interface device including the same.

According to some example embodiments of the inventive concept, an input device includes: a housing in which a transmissive portion is defined; a communicator in the housing and configured to transmit or receive (e.g., exchanged) a signal externally; a pressure sensor in the housing along an inner circumferential surface of the housing; and a measurement sensor in the housing and facing the transmissive portion.

According to some embodiments, an opening may be defined in a portion of the pressure sensor facing the transmissive portion.

According to some embodiments, a portion of the housing facing the pressure sensor may include rubber or plastic.

According to some embodiments, the input device may further include a support part spaced apart from the inner circumferential surface of the housing with the pressure sensor therebetween.

According to some embodiments, the support part may include a first portion having a shape conforming to a shape of the inner circumferential surface of the housing and a second portion surrounded by the first portion and reinforcing the first portion.

According to some embodiments, the pressure sensor may be a film-type pressure sensor and may be flexible.

According to some embodiments, the pressure sensor may be transparent.

According to some embodiments, the measurement sensor may include a light emitter configured to provide light and a light receiver configured to detected reflected light.

According to some embodiments, the light emitter may include at least one of an infrared light source for emitting infrared light or a red light source for emitting red light, and the light receiver may be a photodiode.

According to some embodiments, the measurement sensor may be a photoplethysmography sensor, and may measure at least one of a blood pressure, oxygen saturation, or heart rate of a user.

According to some embodiments, the input device may further include a display configured to display information obtained from the pressure sensor and the measurement sensor.

According to some embodiments, the input device may be an active pen, and the communicator may receive an uplink signal externally and output a downlink signal.

According to some embodiments of the inventive concept, an interface device includes: a display device including a display layer and a sensor layer on the display layer; and an input device configured to receive an uplink signal from the sensor layer and output a downlink signal to the sensor layer, wherein the input device may include a measurement sensor and a pressure sensor for measuring a blood pressure of a user.

According to some embodiments, the input device may include: a housing in which a transmissive portion is defined; a support part in the housing; a communicator in the housing and configured to receive the uplink signal and transmit the downlink signal; and an electrode electrically connected to the communicator, wherein the pressure sensor and the measurement sensor are in the housing.

According to some embodiments, the measurement sensor may be facing the transmissive portion.

According to some embodiments, the pressure sensor may be arranged along an inner circumferential surface of the housing, and an opening may be defined in a portion of the pressure sensor facing the transmissive portion.

According to some embodiments, the pressure sensor may be between the housing and the support part, and the support part may include a first portion having a shape conforming to a shape of an inner circumferential surface of the housing and a second portion surrounded by the first portion and reinforcing the first portion.

According to some embodiments, a portion of the housing facing the pressure sensor may include rubber or plastic.

According to some embodiments, the measurement sensor may include a light emitter configured to provide light and a light receiver configured to detected reflected light, wherein the light emitter may include at least one of an infrared light source for emitting infrared light or a red light source for emitting red light, and the light receiver may be a photodiode.

According to some embodiments, the pressure sensor may be a film-type pressure sensor and is flexible.

BRIEF DESCRIPTION OF THE FIGURES

The accompanying drawings are included to provide a further understanding of some embodiments according to the inventive concept, and are incorporated in and constitute a part of this specification. The drawings illustrate aspects of some example embodiments of the inventive concept and, together with the description, serve to explain principles of some embodiments of the inventive concept. In the drawings:

FIG. 2A is a cross-sectional view of a display device according to some embodiments of the inventive concept;

FIG. 2B is a cross-sectional view of a display device according to some embodiments of the inventive concept;

DETAILED DESCRIPTION

Figure 1:
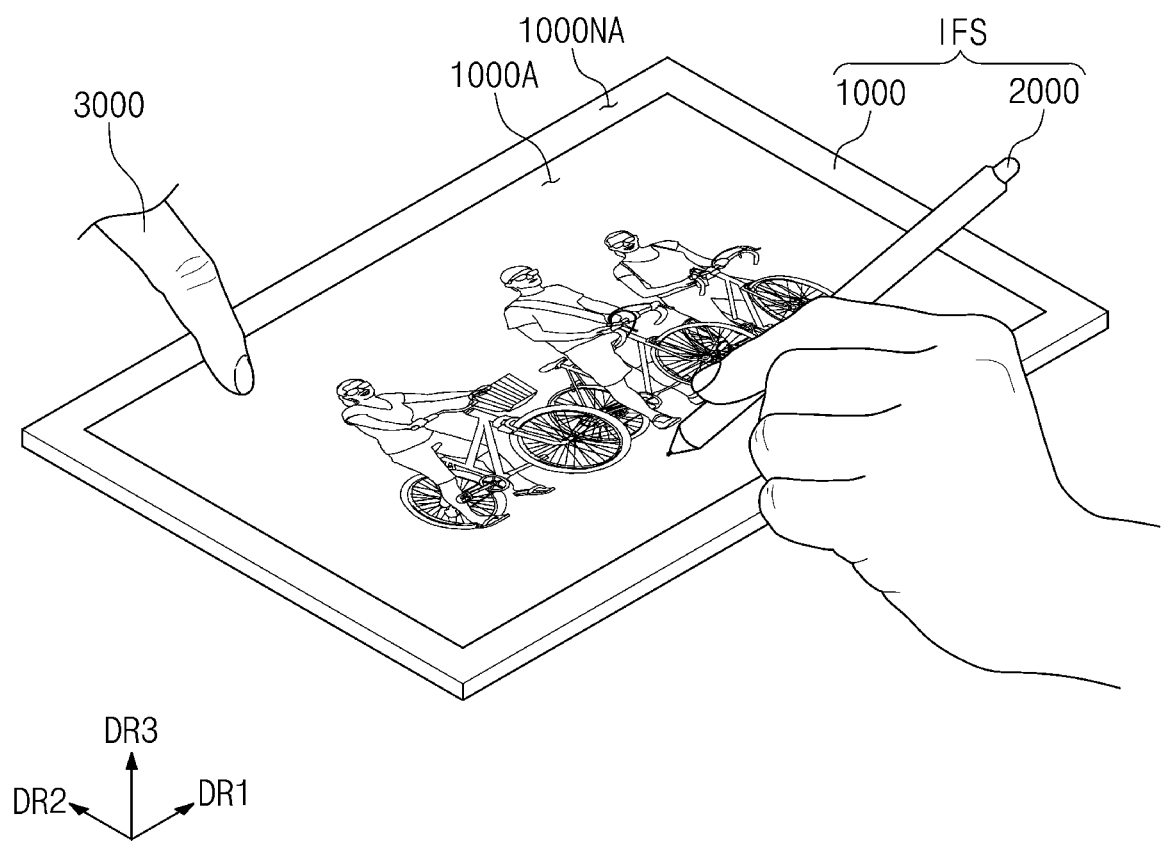
FIG. 1 is a perspective view illustrating an interface device according to some embodiments of the inventive concept.

It will be understood that when an element (or a region, layer, portion, or the like) is referred to as being "on", "connected to", or "coupled to" another element, it can be directly on or directly connected/coupled to the other element, or a third element may be present therebetween.

The same reference numerals refer to the same elements. In the drawings, the thicknesses, ratios, and dimensions of elements are exaggerated for clarity of illustration.

As used herein, the term "and/or" includes any combinations that can be defined by associated elements.

The terms "first", "second" and the like may be used for describing various elements, but the elements should not be construed as being limited by the terms. Such terms are only used for distinguishing one element from other elements. For example, a first element could be termed a second element and vice versa without departing from the teachings of the present disclosure. The terms of a singular form may include plural forms unless otherwise specified.

Furthermore, the terms "under", "lower side", "on", "upper side", and the like are used to describe association relationships among elements illustrated in the drawings. The terms, which are relative concepts, are used on the basis of directions illustrated in the drawings.

All of the terms used herein (including technical and scientific terms) have the same meanings as understood by those skilled in the art, unless otherwise defined. Terms in common usage such as those defined in commonly used dictionaries should be interpreted to contextually match the lexical meanings in the relevant art, and may be explicitly defined herein unless interpreted in an idealized or overly formal sense.

It will be further understood that the terms "include", "including", "has", "having", and the like, when used in this specification, specify the presence of stated features, numbers, steps, operations, elements, components, or combinations thereof, but do not preclude the presence or addition of one or more other features, numbers, steps, operations, elements, components, or combinations thereof.

The terms "part" and "unit" represent a software component or hardware component for performing a specific function. The hardware component may include, for example, a field-programmable gate array (FPGA) or an application-specific integrated circuit (ASIC). The software component may refer to executable codes and/or data used by executable codes in an addressable storage medium. Thus, software components may be, for example, object-oriented software components, class components, and task components, and may include processes, functions, attributes, procedures, sub routines, program code segments, drivers, pieces of firmware, micro codes, circuits, data, databases, data structures, tables, arrays, or variables.

Hereinafter, embodiments of the inventive concept will be described in more detail with reference to the accompanying drawings.

FIG. 1 is a perspective view illustrating an interface device according to some embodiments of the inventive concept.

Referring to FIG. 1, an interface device IFS may include a display device 1000 and an input device 2000. The display device 1000 may detect an input from the input device 2000. In the present disclosure, the display device 1000 and the input device 2000 are referred to as the interface device IFS. The interface device IFS may be referred to as an electronic system, a touch system, an input/output system, a pen tablet, or a pen terminal.

The electronic device 1000 may be a device which is activated in response to an electric signal. For example, the display device 1000 may be a mobile phone, a foldable phone, a tablet, a vehicle navigation device, a game machine, or a wearable device, but is not limited thereto. FIG. 1 illustrates an example of the display device 1000 as a tablet according to some embodiments.

In the display device 1000, an active region 1000A, where images are displayed, and a peripheral region 1000NA, outside a periphery of the active region 1000A, may be defined. The display device 1000 may display an image through the active region 1000A. The active region 1000A may include a surface defined by a first direction DR1 and a second direction DR2. The peripheral region 1000NA may surround the active region 1000A.

A thickness direction of the display device 1000 may be parallel with a third direction DR3 intersecting with the first direction DR1 and the second direction DR2. Therefore, front surfaces (or top surfaces) and rear surfaces (or bottom surfaces) of members constituting the display device 1000 may be defined based on the third direction DR3.

The display device 1000 may detect inputs applied from the outside of the display device 1000. For example, the display device 1000 may detect a first input generated by the input device 2000 and a second input generated by a touch 3000. The input device 2000, which is an active-type input unit for providing a driving signal, may be an active pen. The touch 3000 may include any input means capable of causing a change in a capacitance, such as a user's body or a passive pen.

The display device 1000 and the input device 2000 may communicate with each other bidirectionally. The display device 1000 may provide an uplink signal to the input device 2000, and the input device 2000 may provide a downlink signal to the display device 1000. For example, the uplink signal may include panel information, protocol version information, or the like, but is not particularly limited thereto. The downlink signal may include a synchronization signal or state information about the input device 2000. For example, the downlink signal may include coordinate information about the input device 2000, battery information about the input device 2000, tilt information about the input device 2000, and/or a variety of information stored in the input device 2000, but is not particularly limited thereto.

FIG. 2A is a cross-sectional view of a display device according to some embodiments of the inventive concept.

Referring to FIG. 2A, the display device 1000 may include a display layer 100 and a sensor layer 200.

The display layer 100 may substantially generate an image. The display layer 100 may be an emissive display layer, for example, may be an organic light-emitting layer, a quantum dot display layer, a micro LED display layer, or a nano LED display layer.

The display layer 100 may include a base layer 110, a circuit layer 120, an light-emitting element layer 130, and an encapsulation layer 140.

The base layer 110 may be a member that provides a base surface on which the circuit layer 120 is located. The base layer 110 may be a glass substrate, a metal substrate, a polymer substrate, or the like. However, embodiments according to the present disclosure are not limited thereto, and, thus, the base layer 110 may be an inorganic layer, an organic layer, or a composite material layer.

The base layer 110 may have a multi-layer structure. For example, the base layer 110 may include a first synthetic resin layer, a silicon oxide (SiOx) layer located on the first synthetic resin layer, an amorphous silicon (a-Si) layer located on the silicon oxide layer, and a second synthetic resin layer located on the amorphous silicon layer. The silicon oxide layer and the amorphous silicon layer may be referred to as a base barrier layer.

Each of the first and second synthetic resin layers may include a polyimide-based resin. Furthermore, each of the first and second synthetic resin layers may include at least one of acrylate-based resin, methacrylate-based resin, polyisoprene-based resin, vinyl-based resin, epoxy-based resin, urethane-based resin, cellulose-based resin, siloxane-based resin, polyamide-based resin, or perylene-based resin. Herein, the term " . . . -based resin" indicates inclusion of a functional group of " . . . ".

The circuit layer 120 may be located on the base layer 110. The circuit layer 120 may include an insulating layer, a semiconductor pattern, a conductive pattern, a signal line, and the like. An insulating layer, a semiconductor layer, and a conductive layer may be formed on the base layer 110 through coating, deposition, or the like, and, thereafter, the insulating layer, the semiconductor layer, and the conductive layer may be selectively patterned by repeating a photolithography process multiple times. Thereafter, a semiconductor pattern, a conductive pattern, and a signal line may be formed in the circuit layer 120.

The light-emitting element layer 130 may be located on the circuit layer 120. The light-emitting element layer 130 may include a light-emitting element. For example, the light-emitting element layer 130 may include an organic luminescent material, quantum dot, quantum rod, micro LED, or nano LED.

The encapsulation layer 140 may be located on the light-emitting element layer 130. The inorganic layer 140 may protect the light-emitting element layer 130 from moisture, oxygen, and foreign matter such as dust particles.

The sensor layer 200 may be located on the display layer 100. The sensor layer 200 may detect an external input applied externally. The external input may be a user's input. The user's input may include various types of external inputs such as a part of a user's body, light, heat, pen, or pressure.

The sensor layer 200 may be formed on the display layer 100 through a continuous process. In this case, the sensor layer 200 may be referred to as being directly located on the display layer 100. Being directly located may indicate that a third component is not located between the sensor layer 200 and the display layer 100. That is, an additional adhesive member may not be located between the sensor layer 200 and the display layer 100.

Alternatively, the sensor layer 200 may be bonded to the display layer 100 through an adhesive member. The adhesive member may include a typical adhesive or removable adhesive.

According to some embodiments, the display device 1000 may further include an anti-reflection layer and an optical layer located on the sensor layer 200. The anti-reflection layer may reduce reflexibility of external light incident from the outside of the display device 1000. The optical layer may improve a front luminance of the display device 1000 by controlling a direction of light incident from the display layer 1000.

FIG. 2B is a cross-sectional view of a display device according to some embodiments of the inventive concept.

Referring to FIG. 2B, a display device 1000_1 may include a display layer 100_1 and a sensor layer 200_1. The display layer 100_1 may include a base substrate 110_1, a circuit layer 120_1, a light-emitting element layer 130_1, an encapsulation substrate 140_1, and a bonding member 150_1.

Each of the base substrate 110_1 and the encapsulation layer 140_1 may be a glass substrate, a metal substrate, or a polymer substrate, but is not particularly limited thereto.

The bonding member 150_1 may be located between the base substrate 110_1 and the encapsulation substrate 140_1. The bonding member 150_1 may bond the encapsulation substrate 140_1 to the base substrate 110_1 or the circuit layer 120_1. The bonding member 150_1 may include an inorganic material or organic material. For example, the inorganic material may include a frit seal, and the organic material may include photocurable resin or photoplastic resin. However, the material of the bonding member 150_1 is not limited to the above-mentioned example.

The sensor layer 200_1 may be directly located on the encapsulation substrate 140_1. Being "directly located" may indicate that a third component is not located between the sensor layer 200_1 and the encapsulation substrate layer 140_1. That is, an additional adhesive member may not be located between the sensor layer 200_1 and the display layer 100_1. However, embodiments according to the inventive concept are not limited thereto, and, thus, an adhesive layer may be further located between the sensor layer 200_1 and the encapsulation substrate 140_1.

Figure 3:
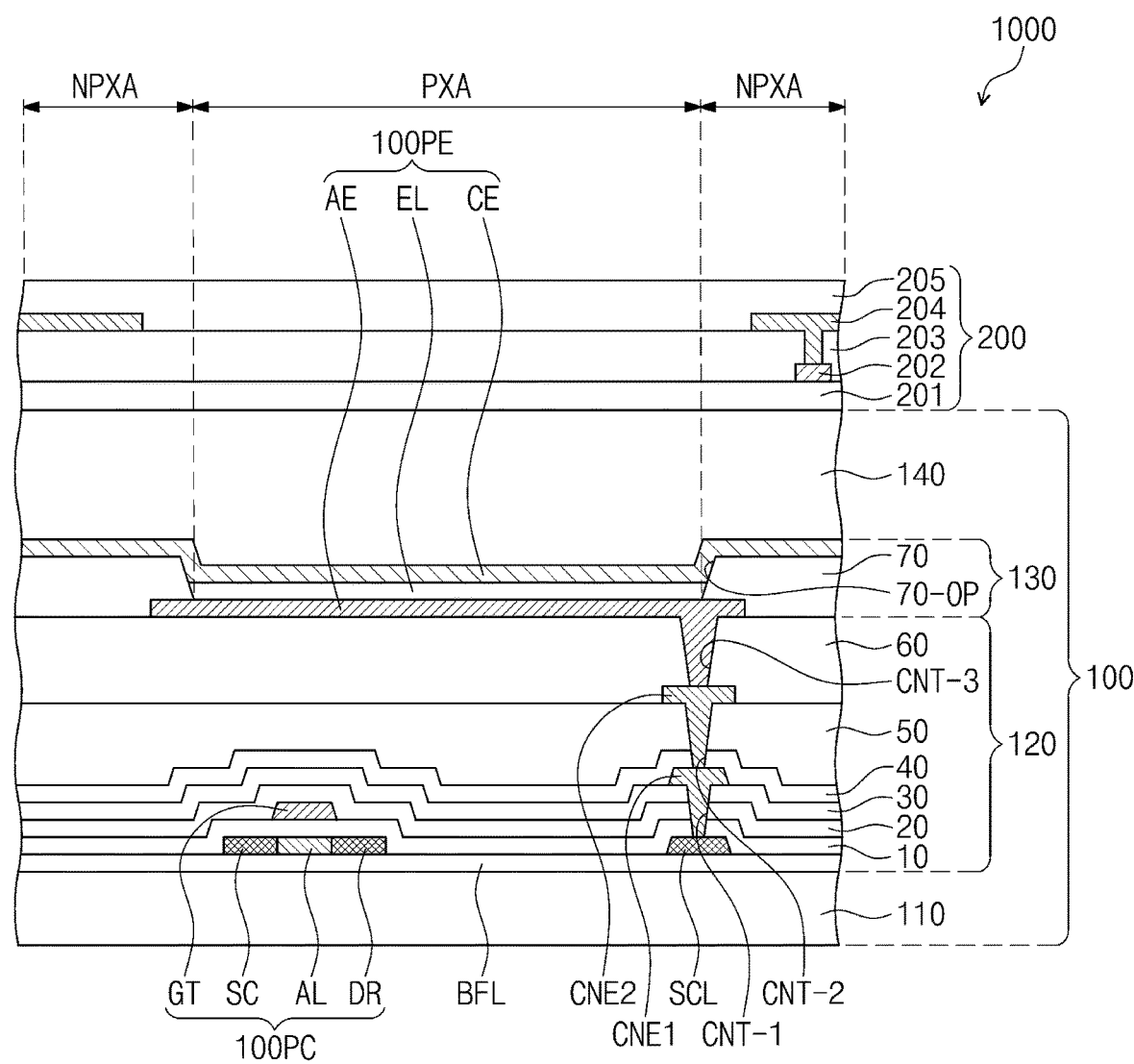
FIG. 3 is a cross-sectional view of a display device according to some embodiments of the inventive concept.

FIG. 3 is a cross-sectional view of a display device according to some embodiments of the inventive concept.

Referring to FIG. 3, at least one inorganic layer is formed on an upper surface of the base layer 110. The inorganic layer may include at least one of aluminum oxide, titanium oxide, silicon oxide, silicon nitride, silicon oxynitride, zirconium oxide, or hafnium oxide. The inorganic layer may be formed as a multi-layer. Inorganic layers of the multi-layer may form a barrier layer and/or a buffer layer. As illustrated in FIG. 3, the display layer 100 may include a buffer layer BFL.

The buffer layer BFL may improve a bonding force between the base layer 110 and the semiconductor pattern. The buffer layer BFL may include at least one of silicon oxide, silicon nitride, or silicon oxynitride. For example, the buffer layer BFL may include a structure in which silicon oxide layers and silicon nitride layers are alternately laminated.

The semiconductor pattern may be located on the buffer layer BFL. The semiconductor pattern may include polysilicon. However, embodiments according to the inventive concept are not limited thereto, and, thus, the semiconductor pattern may include amorphous silicon, low-temperature polycrystalline silicon, or oxide semiconductor.

FIG. 3 only illustrates a partial semiconductor pattern, and another semiconductor pattern may be further located in another region. The semiconductor patterns may be arranged over pixels according to a particular rule. The semiconductor patterns may have different electric properties according to whether the semiconductor patterns are doped. The semiconductor patterns may include a first region having high conductivity and a second region having low conductivity. The first region may be doped with an N-type dopant or P-type dopant. A P-type transistor may include a doped region doped with a P-type dopant, and an N-type transistor may include a doped region doped with an N-type dopant. The second region may be a non-doped region or a region doped at a lower concentration than that of the first region.

The first region may have higher conductivity than that of the second region, and may substantially serve as an electrode or a signal line. The second region may substantially correspond to an active (or channel) of a transistor. In other words, a portion of the semiconductor pattern may be an active of a transistor, another portion may be a source or drain of the transistor, and another portion may be a connection electrode or a connection signal line.

Each of pixels may have an equivalent circuit including seven transistors, one capacitor, and a light-emitting element, and an equivalent circuit diagram of the pixel may be modified into various forms. FIG. 3 illustrates an example of one transistor 100PC and one light-emitting element 100PE included in a pixel.

A source SC, an active AL, and a drain DR of the transistor 100PC may be formed from a semiconductor pattern. The source SC and the drain DR may extend in opposite directions from the active AL in a cross-sectional view. FIG. 3 illustrates a portion of a connection signal line SCL formed from the semiconductor pattern. According to some embodiments, the connection signal line SCL may be connected to the drain DR of the transistor 100PC in a plan view.

A first insulating layer 10 may be located on the buffer layer BFL. The first insulating layer 10 may commonly overlap a plurality of pixels, and may cover the semiconductor pattern. The first insulating layer 10 may be an inorganic layer and/or organic layer, and may have a single-layer or multi-layer structure. The first insulating layer 10 may include at least one of aluminum oxide, titanium oxide, silicon oxide, silicon nitride, silicon oxynitride, zirconium oxide, or hafnium oxide. According to some embodiments, the first insulating layer 10 may be a single layer of a silicon oxide layer. Not only the first insulating layer 10 but also the insulating layer of the circuit layer 120 described below may be an inorganic layer and/or organic layer, and may have a single-layer or multi-layer structure. The inorganic layer may include at least one of the above-mentioned materials, but embodiments according to the present disclosure are not limited thereto.

A gate GT of the transistor 100PC is located on the first insulating layer 10. The gate GT may be a portion of a metal pattern. The gate GT overlaps the active AL. The gate GT may function as a mask during a process of doping a semiconductor pattern.

A second insulating layer 20 may be located on the first insulating layer 10, and may cover the gate GT. The second insulating layer 20 may commonly overlap pixels. The second insulating layer 20 may be an inorganic layer and/or organic layer, and may have a single-layer or multi-layer structure. The second insulating layer 20 may include at least one of silicon oxide, silicon nitride, or silicon oxynitride. According to some embodiments, the second insulating layer 20 may have a multi-layer structure including a silicon oxide layer and a silicon nitride layer.

A third insulating layer 30 may be located on the second insulating layer 20. The third insulating layer 30 may have a single-layer or multi-layer structure. For example, the third insulating layer 30 may have a multi-layer structure including a silicon oxide layer and a silicon nitride layer.

A first connection electrode CNE1 may be located on the third insulating layer 30. The first connection electrode CNE1 may be connected to the connection signal line SCL through a contact hole CNT-1 penetrating the first to third insulating layers 10, 20, and 30.

A fourth insulating layer 40 may be located on the third insulating layer 30. The fourth insulating layer 40 may be a single layer of a silicon oxide layer. A fifth insulating layer 50 may be located on the fourth insulating layer 40. The fifth insulating layer 50 may be an organic layer.

A second connection electrode CNE2 may be located on the fifth insulating layer 50. The second connection electrode CNE2 may be connected to the first connection electrode CNE1 through a contact hole CNT-2 penetrating the fourth insulating layer 40 and the fifth insulating layer 50.

A sixth insulating layer 60 may be located on the fifth insulating layer 50, and may cover the second connection electrode CNE2. The sixth insulating layer 60 may be an organic layer.

The light-emitting element layer 130 may be located on the circuit layer 120. The light-emitting element layer 130 may include the light-emitting element 100PE. For example, the light-emitting element layer 130 may include an organic luminescent material, quantum dot, quantum rod, micro LED, or nano LED. Hereinafter, the light-emitting element 100PE will be described as an organic light-emitting element, but is not particularly limited thereto.

The light-emitting element 100PE may include a first electrode AE, an emission layer EL, and a second electrode CE.

The first electrode AE may be located on the sixth insulating layer 60. The first electrode AE may be connected to the second connection electrode CNE2 through a contact hole CNT-3 penetrating the sixth insulating layer 60.

A pixel defining layer 70 may be located on the sixth insulating layer 60, and may cover a portion of the first electrode AE. An opening 70-OP is defined in the pixel defining layer 70. The opening 70-OP of the pixel defining layer 70 exposes at least a portion of the first electrode AE.

The active region 1000A (see FIG. 1) may include an emission region PXA and a non-emission region NPXA adjacent to the emission region PXA. The non-emission region NPXA may surround the emission region PXA. According to some embodiments, the emission region PXA is defined to correspond to a partial region of the first electrode AE exposed by the opening 70-OP.

The emission layer EL may be located on the first electrode AE. The emission layer EL may be located in a region corresponding to the opening 70-OP. That is, the emission layer EL may be separately formed in each pixel. In the case where the emission layer EL is separately formed in each pixel, each of the emission layers EL may emit light having at least one of blue color, red color, or green color. However, embodiments according to the inventive concept are not limited thereto, and the emission layer EL may be connected to pixels so as to be commonly provided to the pixels. In this case, the emission layer EL may provide blue light or white light.

The second electrode CE may be located on the emission layer EL. The second electrode CE may have a shape of a single body, and may be formed commonly in a plurality of pixels.

According to some example embodiments, a hole control layer may be located between the first electrode AE and the emission layer EL. The hole control layer may be formed commonly in the emission region PXA and the non-emission region NPXA. The hole control layer may include a hole transport layer, and may further include a hole injection layer. An electron control layer may be located between the emission layer EL and the second electrode CE. The electron control layer may include an electron transport layer, and may further include an electron injection layer. The hole control layer and the electron control layer may be formed commonly in a plurality of pixels using an open mask.

The encapsulation layer 140 may be located on the light-emitting element layer 130. The encapsulation layer 140 may include an inorganic layer, organic layer, and inorganic layer staked sequentially, but layers constituting the encapsulation layer 140 are not limited thereto.

The inorganic layers may protect the light-emitting element layer 130 from moisture and oxygen, and the organic layer may protect the light-emitting element 130 from foreign matter such as dust particles. The inorganic layers may include a silicon nitride layer, a silicon oxynitride layer, a silicon oxide layer, a titanium oxide layer, an aluminum oxide layer, or the like. The organic layer may include an acryl-based organic layer, but is not limited thereto.

The sensor layer 200 may include a base layer 201, a first conductive layer 202, a detection insulating layer 203, a second conductive layer 204, and a cover insulating layer 205.

The base layer 201 may be an inorganic layer including at least one of silicon nitride, silicon oxynitride, or silicon oxide. Alternatively, the base layer 201 may be an organic layer including epoxy resin, acryl resin, or imide-based resin. The base layer 201 may have a single-layer structure, or may have a multi-layer structure laminated along the third direction DR3.

Each of the first conductive layer 202 and the second conductive layer 204 may have a single-layer structure, or may have a multi-layer structure laminated along the third direction DR3.

A conductive layer having a single-layer structure may include a metal layer or a transparent conductive layer. The metal layer may include molybdenum, silver, titanium, copper, aluminum, or an alloy thereof. The transparent conductive layer may include a transparent conductive oxide such as indium tin oxide (ITO), indium zinc oxide (IZO), zinc oxide (ZnO), and indium zinc tin oxide (IZTO). In addition, the transparent conductive layer may include a conductive polymer such as PEDOT, metal nanowire, graphene, or the like.

A conductive layer having a multi-layer structure may include metal layers. The metal layers may have, for example, a triple-layer structure of titanium/aluminum/titanium. The conductive layer having a multi-layer structure may include at least one metal layer and at least one transparent conductive layer.

At least one of the detection insulating layer 203 or the cover insulating layer 205 may include an inorganic layer. The inorganic layer may include at least one of aluminum oxide, titanium oxide, silicon oxide, silicon nitride, silicon oxynitride, zirconium oxide, or hafnium oxide.

At least one of the detection insulating layer 203 or the cover insulating layer 205 may include an organic layer. The organic layer may include at least one of acrylic resin, methacrylic resin, polyisoprene, vinyl-based resin, epoxy-based resin, urethane-based resin, cellulosic resin, siloxane-based resin, polyimide-based resin, polyamide-based resin, or perylene-based resin.

Figure 4:
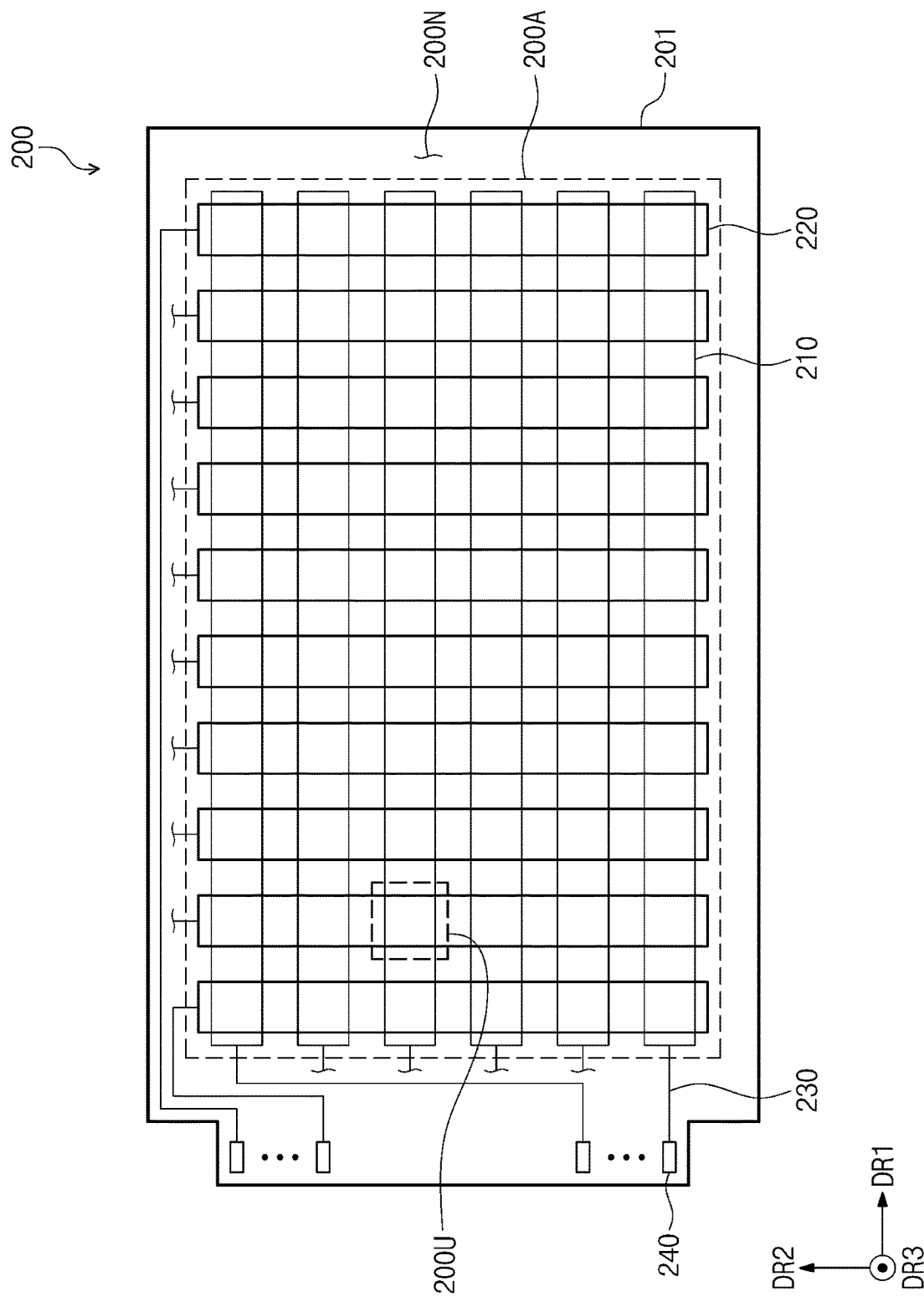
FIG. 4 is a planar view illustrating a sensor layer according to some embodiments of the inventive concept.

FIG. 4 is a planar view illustrating a sensor layer according to some embodiments of the inventive concept.

Referring to FIG. 4, a detection region 200A and a peripheral region 200N may be defined in the sensor layer 200. The detection region 200A may correspond to the active region 1000A illustrated in FIG. 1, and the peripheral region 200N may correspond to the peripheral region 1000NA illustrated in FIG. 1.

The sensor layer 200 may include electrodes 210, intersecting electrodes 220, lines 230, and pads 240.

Each of the electrodes 210 may extend in the first direction DR1, and the electrodes 210 may be arranged in the second direction DR2 with a spacing therebetween. Each of the intersecting electrodes 220 may extend in the second direction DR2, and the intersecting electrodes 220 may be arranged in the first direction DR1 with a spacing therebetween.

Each of the electrodes 210 and the intersecting electrodes 220 may be electrically connected to a corresponding line among the lines 230. Although FIG. 4 illustrates an example of a single routing structure in which one electrode 210 is connected to one line 230, and one intersecting electrode 220 is connected to one line 230, embodiments of the inventive concept are not particularly limited thereto. For example, two lines 230 may be connected to each of the intersecting electrodes 220. Alternatively, two lines 230 may be connected to each of the electrodes 210, and two lines 230 may also be connected to each of the intersecting electrodes 220.

The pads 240 may be electrically connected to the lines 230 respectively. The sensor layer 200 may be electrically connected to a sensor driver 200C (see FIG. 5A) through the pads 240.

Figure 5A:
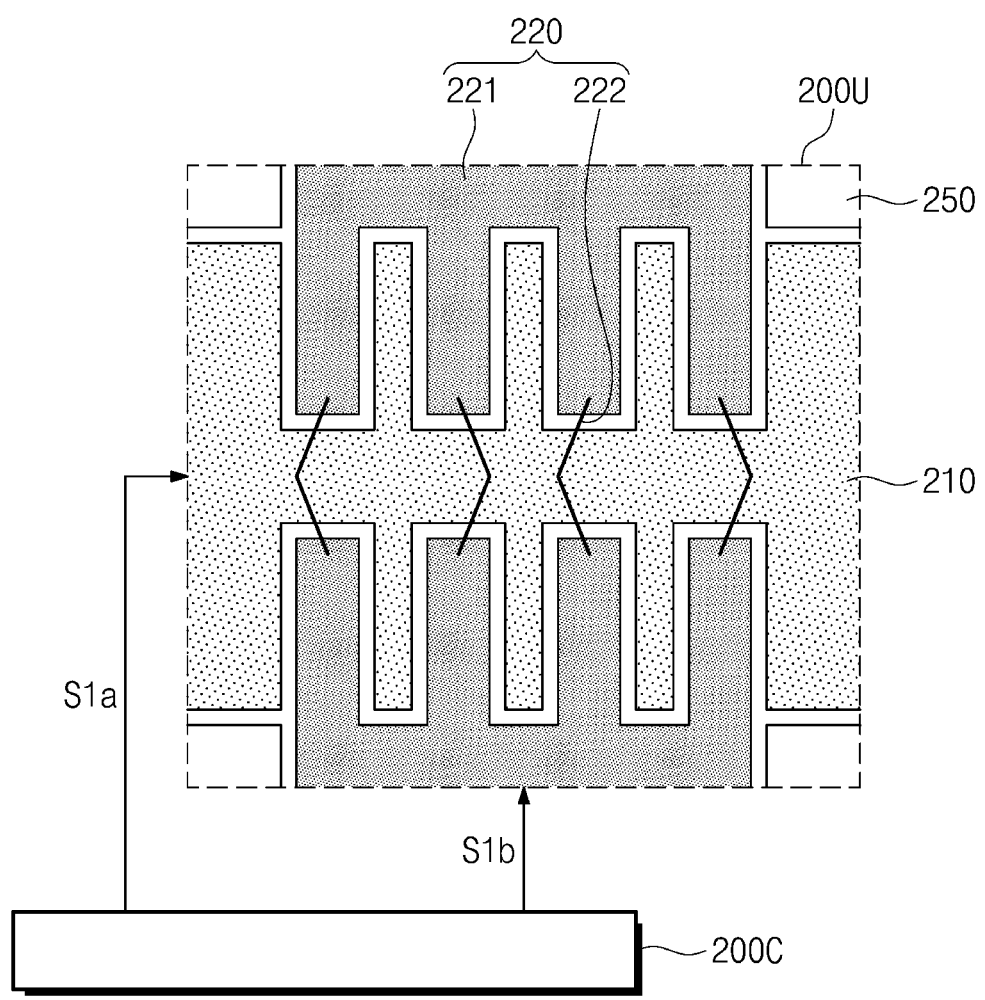
FIGS. 5A and 5B are diagrams for describing a first mode operation of a sensor layer according to some embodiments.
Figure 5B:
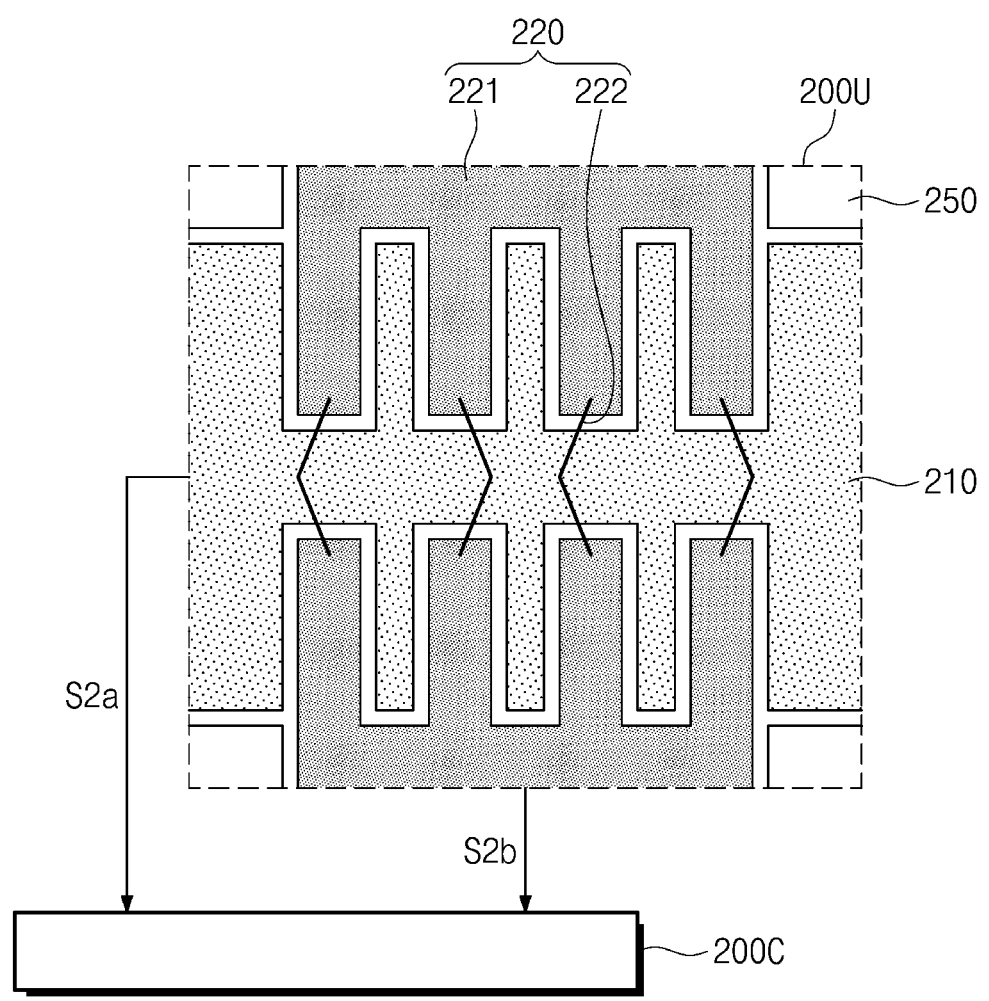

FIGS. 5A and 5B are diagrams for describing a first mode operation of a sensor layer.

Referring to FIGS. 4, 5A, and 5B, a portion of one electrode 210 and a portion of one intersecting electrode 220 may be defined as one sensing unit 200U. Each of FIGS. 5A and 5B illustrates one enlarged sensing unit 200U.

The intersecting electrode 220 may include intersecting patterns 221 and bridge patterns 222 electrically connected to the intersecting patterns 221. The intersecting patterns 221 may be spaced apart from each other with the electrode 210 therebetween. The bridge patterns 222 may overlap the electrode 210, and may insulatively intersect with the electrode 210.

The intersecting patterns 221 and the electrode 210 may be formed in the same layer, and the bridge patterns 222 may be formed in a layer different from the layer of the intersecting patterns 221 and the electrode 210. For example, the intersecting patterns 221 and the electrode 210 may be included in the second conductive layer 204 (see FIG. 3), and the bridge patterns 222 may be included in the first conductive layer 202 (see FIG. 3), and this structure may be referred to as a bottom bridge structure. However, embodiments according to the inventive concept are not particularly limited thereto. For example, the intersecting patterns 221 and the electrode 210 may be included in the first conductive layer 202 (see FIG. 3), and the bridge patterns 222 may be included in the second conductive layer 204 (see FIG. 3), and this structure may be referred to as a top bridge structure.

Furthermore, the sensor layer 200 may further include a dummy pattern 250 located in a region in which the intersecting patterns 221 and the electrode 210 are not located. The dummy pattern 250 may be provided to prevent the electrode 210 and the intersecting electrode 220 from being viewed from the outside, and may be an electrically floated pattern. The dummy pattern 250 may be referred to as a floating pattern or a pattern.

Each of the intersecting patterns 221, the electrode 210, and the dummy pattern 250 may have a mesh structure. In this case, an opening may be defined in each of the intersecting patterns 221, the electrode 210, and the dummy pattern 250. However, embodiments according to the inventive concept are not limited thereto, and each of the intersecting patterns 221, the electrode 210, and the dummy pattern 250 may be configured as a transparent cylindrical electrode.

Referring to FIGS. 5A and 5B, the first mode may be a mode in which the display device 1000 (see FIG. 1) and the input device 2000 (see FIG. 1) transmit/receive data to/from each other. The operation illustrated in FIG. 5A may be an operation of providing an uplink signal from the display device 1000 (see FIG. 1) to the input device 2000 (see FIG. 1). The operation illustrated in FIG. 5B may be an operation of providing a downlink signal from the input device 2000 (see FIG. 1) to the display device 1000 (see FIG. 1).

Referring to FIG. 5A, each of the electrode 210 and the intersecting electrode 220 may be used as a transmission electrode for providing uplink signals S1a and S1b provided from the sensor driver 200C to the input device 2000 (see FIG. 1). Although FIG. 5A illustrates an example in which both the electrode 210 and the intersecting electrode 220 are used as a transmission electrode, embodiments according to the inventive concept are not particularly limited thereto. For example, the electrode 210 or the intersecting electrode 220 may be used as a transmission electrode.

Referring to FIG. 5B, each of the electrode 210 and the intersecting electrode 220 may be used a reception electrode for transferring detection signals S2a and S2b induced from the input device 2000 (see FIG. 1) to the sensor driver 200C.

The sensor driver 200C may receive a first detection signal S2a from the electrode 210, and may receive a second detection signal S2b from the intersecting electrode 220.

Figure 6:
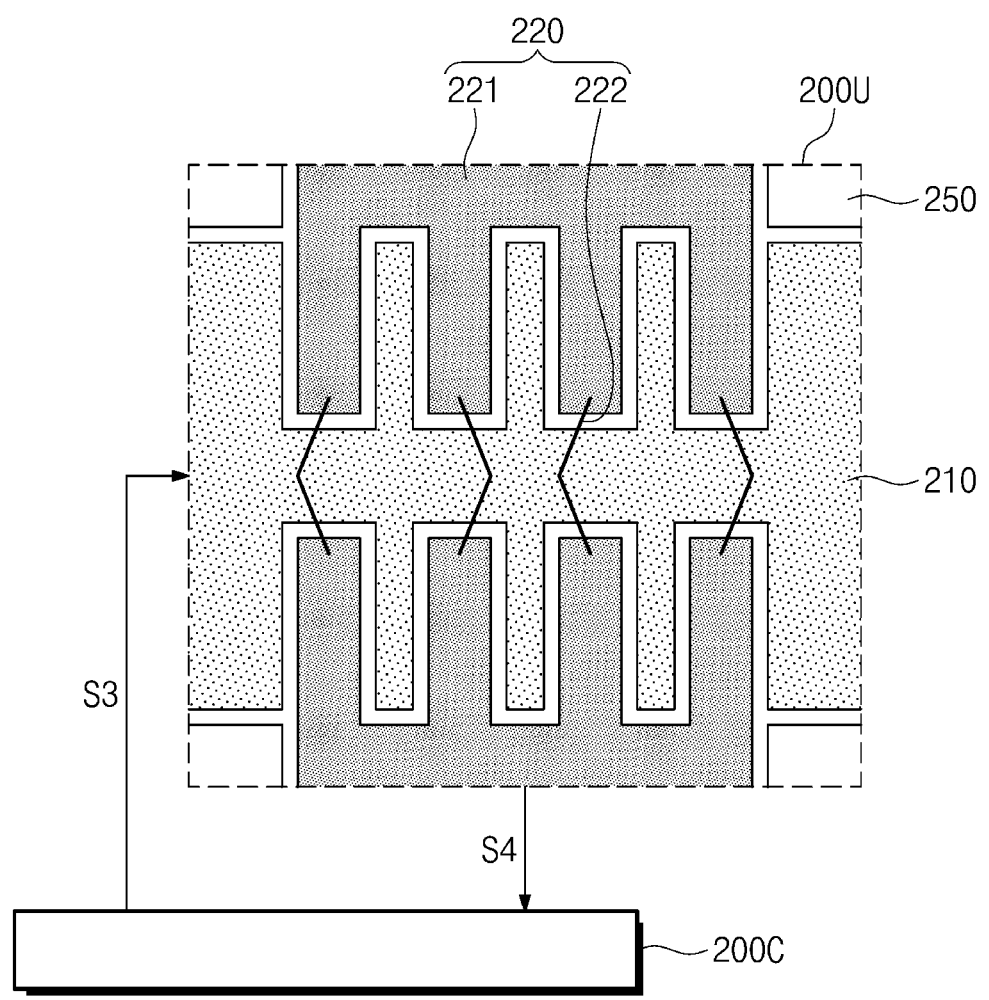
FIG. 6 is a diagram for describing a second mode operation of a sensor layer according to some embodiments.

FIG. 6 is a diagram for describing a second mode operation of a sensor layer.

Referring to FIGS. 4 and 6, the sensor driver 200C may detect a second input generated by the touch 3000 (see FIG. 1) in a second mode. In the second mode, the sensor driver 200C may detect an external input by detecting a variation in mutual capacitance formed between the electrode 210 and the intersecting electrode 220.

The sensor driver 200C may provide a driving signal S3 to the electrode 210, and may receive a detection signal S4 from the intersecting electrode 220. That is, in the second mode, the electrode 210 may function as a transmission electrode, and the intersecting electrode 220 may function as a reception electrode. However, embodiments according to the inventive concept are not particularly limited thereto. For example, the electrode 210 may function as a reception electrode, and the intersecting electrode 220 may function as a transmission electrode.

Figure 7:
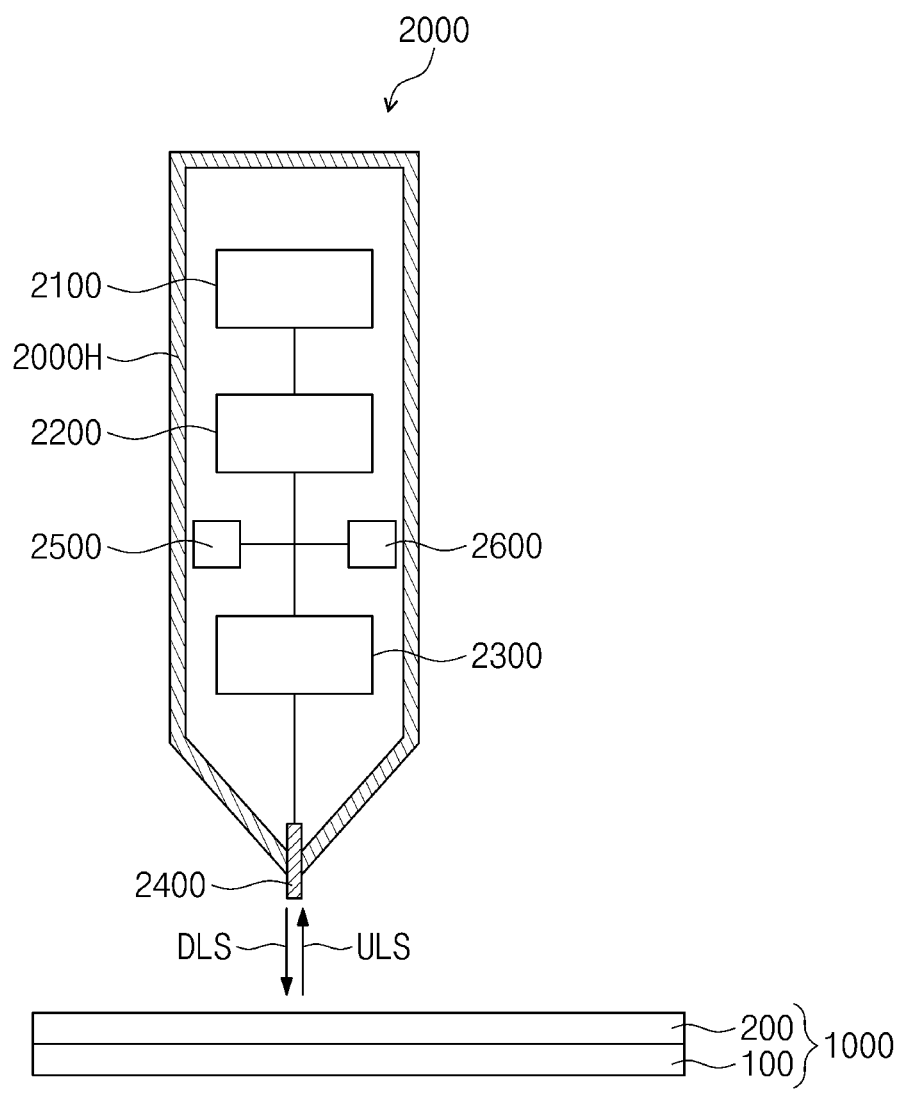
FIG. 7 is a block diagram illustrating an input device according to some embodiments of the inventive concept.

FIG. 7 is a block diagram illustrating an input device according to some embodiments of the inventive concept.

Referring to FIG. 7, the input device 2000 may include a housing 2000H, a power supply 2100, a controller 2200, a communicator 2300, an electrode 2400, a measurement sensor 2500, and a pressure sensor 2600. However, components of the input device 2000 are not limited to the above components. For example, the input device 2000 may further include an electrode switch for switching to a signal transmission mode or a signal reception mode, a memory for storing information (e.g., set or predetermined information), a rotation sensor for detecting rotation, or the like.

The housing 2000H may have a pen shape, and may have an accommodation space formed therein. The power supply 2100, the controller 2200, the communicator 2300, the electrode 2400, the measurement sensor 2500, and the pressure sensor 2600 may be accommodated in the accommodation space defined in the housing 2000H.

The power supply 2100 may supply power to the controller 2200, the communicator 2300, the measurement sensor 2500, and the pressure sensor 2600. The power supply 2100 may include a battery or a high-capacity capacitor.

The controller 2200 may control operation of the input device 2000. The controller 2200 may be an application-specific integrated circuit (ASIC). The controller 2200 may be configured to operate according to a designed program.

The communicator 2300 may include a reception circuit and/or a transmission circuit. The reception circuit may receive an uplink signal ULS provided from the sensor layer 200. The reception circuit may convert the uplink signal ULS into a signal processible by the controller 2200. The transmission circuit may receive a signal provided from the controller 2200 and may convert the signal into a signal sensible by the sensor layer 200. The transmission circuit may output a downlink signal DLS through the electrode 2400. Thus, according to some example embodiments, the communicator 2300 may be configured to receive and/or emit or provide (e.g., exchange) signals for communication with one or more external components or devices.

The electrode 2400 may be referred to as a pen tip. The electrode 2400 may be electrically connected to the communicator 2300. A portion of the electrode 2400 may protrude from the housing 2000H. Alternatively, the input device 2000 may further include a cover housing that covers the electrode 2400 exposed from the housing 2000H. Alternatively, the electrode 2400 may be embedded in the housing 2000H.

The measurement sensor 2500 and the pressure sensor 2600 may be components for measuring biometric information about a user. For example, the measurement sensor 2500 and the pressure sensor 2600 may measure a blood pressure of the user. The measurement sensor 2500 may be a photoplethysmography (PPG) sensor. The pressure sensor 2600 may be a film-type pressure sensor and may be flexible.

The pressure sensor 2600 may obtain a value of a pressure applied to the pressure sensor 2600 and an area of a portion of a user's body which is in contact with the pressure sensor 2600. The measurement sensor 2500 may measure a change in a blood volume (or change in a blood flow rate). The controller 2200 may receive a pressure value from the pressure sensor 2600 and information about a change in a blood volume from the measurement sensor 2500 to recognize a blood pressure of the user.

According to some embodiments of the inventive concept, the blood pressure of the user is measured using the input device 2000. That is, the blood pressure of the user may be easily measured using the pressure sensor 2600 and the measurement sensor 2500 included in the input device 2000 without additional equipment such as a cuff. While the user is performing a task using the input device 2000, the blood pressure of the user may be measured periodically or aperiodically.

When the blood pressure of the user is abnormal, the controller 2200 may transmit information about blood pressure abnormality to the display device 1000 via the communicator 2300. The display device 1000 may display the information about blood pressure abnormality to notify the user of the information about blood pressure abnormality.

Figure 8:
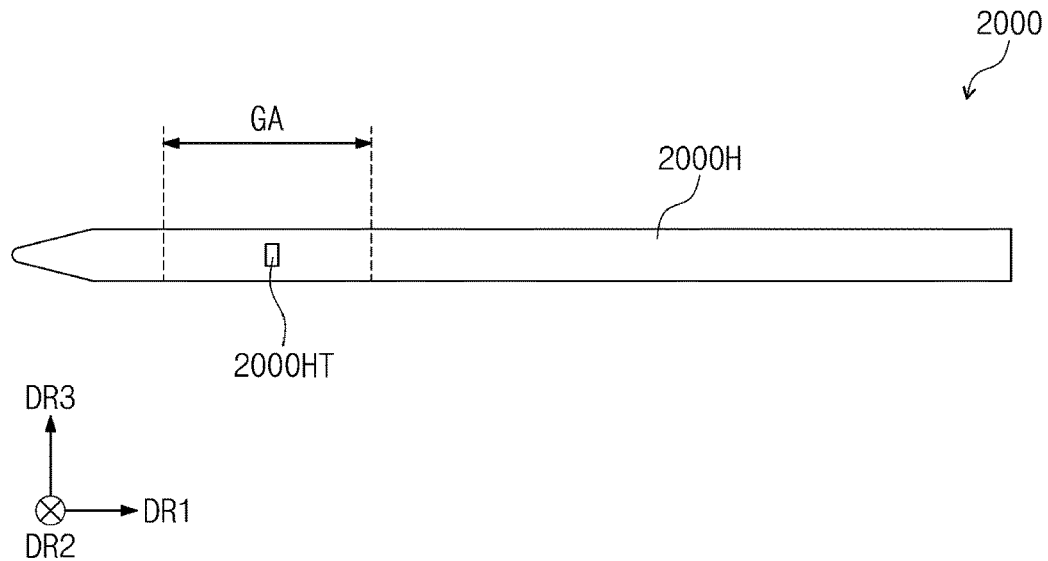
FIG. 8 is a side view of an input device according to some embodiments of the inventive concept.
Figure 9:
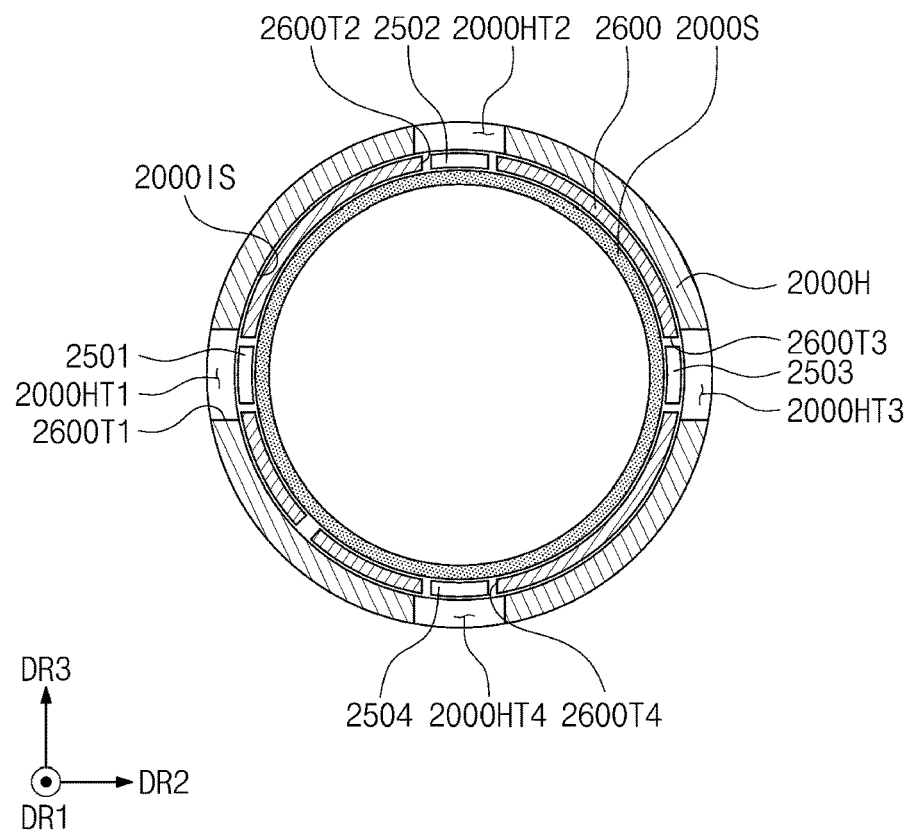
FIG. 9 is a cross-sectional view of an input device according to some embodiments of the inventive concept.

FIG. 8 is a side view of an input device according to some embodiments of the inventive concept. FIG. 9 is a cross-sectional view of an input device according to some embodiments of the inventive concept.

Referring to FIGS. 7, 8, and 9, a transmissive portion 2000HT may be defined in the housing 2000H. The transmissive portion 2000HT may have a transmittance at which light provided from the measurement sensor 2500 and light reflected from the user are able to be transmitted.

A portion of the housing 2000H in which the transmissive portion 2000HT is defined may be defined as a holding portion GA. The holding portion GA may correspond to a region of the input device 2000 which is held by the user when the user uses the input device 2000. The holding portion GA of the housing 2000H may include a deformable material. For example, the holding portion GA of the housing 2000H may include rubber or plastic. Therefore, a pressure applied by the user may be easily transferred to the pressure sensor 2600.

The measurement sensor 2500 may be provided in plurality. For example, the measurement sensor 2500 may include a first measurement sensor 2501, a second measurement sensor 2502, a third measurement sensor 2503, and a fourth measurement sensor 2504. Although the input device 2000 is illustrated as including the first to fourth measurement sensors 2501 to 2504 according to some embodiments, embodiments according to the inventive concept are not particularly limited thereto. For example, the input device 2000 may include one or more measurement sensors.

First to fourth transmissive portions 2000HT1 to 2000HT4 may be defined in the housing 2000H in correspondence with the first to fourth measurement sensors 2501 to 2504. The first to fourth measurement sensors 2501 to 2504 may transmit and receive light through the first to fourth transmissive portions 2000HT1 to 2000HT4 respectively. That is, the first to fourth measurement sensors 2501 to 2504 may be arranged to be facing the first to fourth transmissive portions 2000HT1 to 2000HT4 respectively.

A light transmissive material may be formed in each of the first to fourth transmissive portions 2000HT1 to 2000HT4. For example, a transparent resin, glass, or the like may be formed in the first to fourth transmissive portions 2000HT1 to 2000HT4. However, embodiments according to the inventive concept are not limited thereto, and the first to fourth transmissive portions 2000HT1 to 2000HT4 may be provided as an empty space.

The pressure sensor 2600 may be arranged along an inner circumferential surface 2000IS of the housing 2000H. In a cross-section view, the inner circumferential surface 2000IS of the housing 2000H may have a circular shape. The pressure sensor 2600 may face the inner circumferential surface 2000IS and may be curved along the inner circumferential surface 2000IS. That is, the pressure sensor 2600 may be a flexible film-type sensor. For example, the pressure sensor 2600 may be a conductive polymer-based tactile sensor, but is not particularly limited thereto.

The pressure sensor 2600 may include a pressure sensitive material obtained by mixing a polymer base material with a conductive material having a size of several micrometers to nanometers. The pressure sensitive material may include a quantum tunneling composite (QTC), pressure sensitive rubber, or pressure sensitive ink, but is not particularly limited thereto.

First to fourth openings 2600T1 to 2600T4 may be defined in the pressure sensor 2600 in correspondence with the first to fourth measurement sensors 2501 to 2504. The first to fourth openings 2600T1 to 2600T4 may face the first to fourth transmissive portions 2000HT1 to 2000HT4 respectively.

The first to fourth measurement sensors 2501 to 2504, the first to fourth openings 2600T1 to 2600T4, and the first to fourth transmissive portions 2000HT1 to 2000HT4 may overlap corresponding components.

The input device 2000 may further include a support part 2000S. The support part 2000S may be spaced apart from the inner circumferential surface 2000IS of the housing 2000H with the pressure sensor 2600 therebetween. The support part 2000S may have a shape conforming to the inner circumferential surface 2000IS of the housing 2000H.

The support part 2000S may be a structure that supports the pressure sensor 2600. The support part 2000S may include a material that is harder than that of the holding portion GA of the housing 2000H. For example, the support part 2000S may include polycarbonate, but is not particularly limited thereto. Since the support part 2000S supports the pressure sensor 2600, a pressure sensing accuracy of the pressure sensor 2600 may be further improved.

Figure 10:
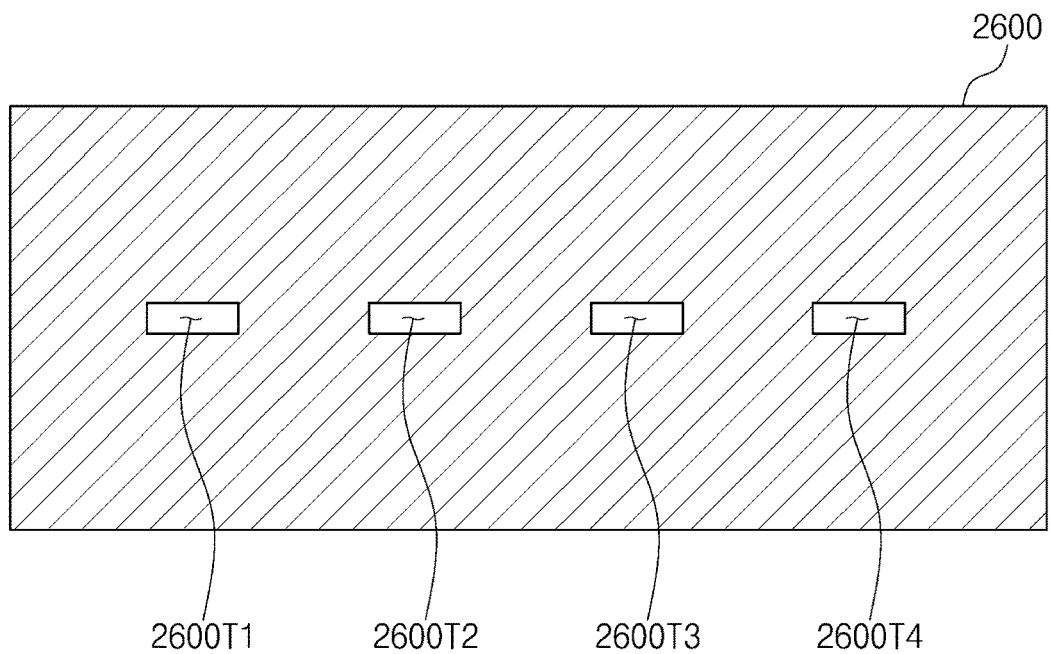
FIG. 10 is a planar view illustrating a pressure sensor according to some embodiments of the inventive concept.

FIG. 10 is a planar view illustrating a pressure sensor according to some embodiments of the inventive concept.

FIG. 10 illustrates the pressure sensor 2600. FIG. 10 illustrates a spread pressure sensor 2600 before the pressure sensor 2600 is accommodated in the housing 2000H (see FIG. 9). Portions of the pressure sensor 2600 may be removed so as to define the first to fourth openings 2600T1 to 2600T4.

Although FIG. 10 illustrates an example in which the first to fourth openings 2600T1 to 2600T4 as being spaced apart in a direction (e.g., a set or predetermined direction), embodiments according to the inventive concept are not limited thereto. For example, the first to fourth openings 2600T1 to 2600T4 may be defined in a form of a two-by-two matrix, and may be variously deformed.

Figure 11:
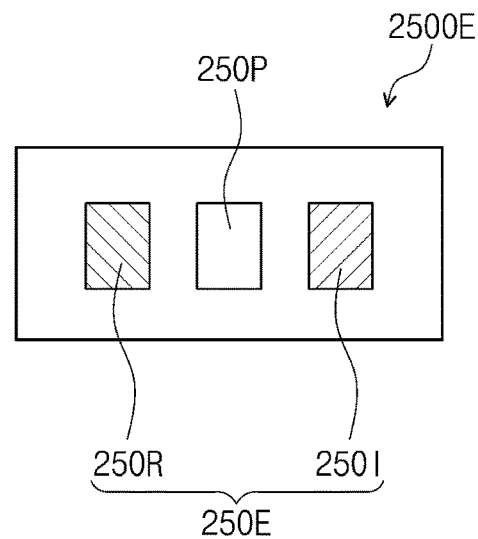
FIG. 11 is a diagram illustrating a measurement sensor according to some embodiments of the inventive concept.

FIG. 11 is a diagram illustrating a measurement sensor according to some embodiments of the inventive concept.

Referring to FIGS. 9 and 11, each of the first to fourth measurement sensors 2501 to 2504 may include a measurement sensor 2500E. The measurement sensor 2500E may include a light emitter 250E and a light receiver 250P. The light emitter 250E may include an infrared light source 2501 for emitting infrared light and a red light source 250R for emitting red light. The light emitter 250P may be a photodiode.

A wavelength of infrared light emitted from the infrared light source 2501 may be about 940 nm, and a wavelength of red light emitted from the red light source 250R may be about 660 nm. Hemoglobin (Hb) in blood may absorb more red light than infrared light. Oxyhemoglobin ($HbO_2$) in blood may absorb more infrared light than red light. Using this characteristic, the input device 2000 (see FIG. 7) may measure not only the blood pressure of the user but also an oxygen saturation and heart rate of the user through the measurement sensor 2500E.

Figure 12A:
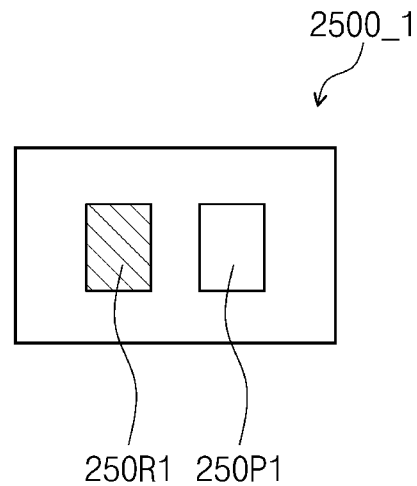
FIGS. 12A and 12B are diagrams illustrating measurement sensors according to some embodiments of the inventive concept.
Figure 12B:
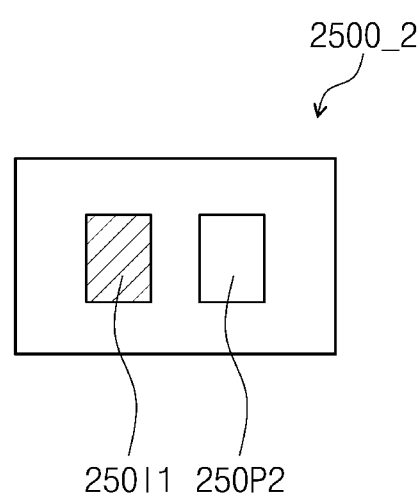

FIGS. 12A and 12B are diagrams illustrating measurement sensors according to some embodiments of the inventive concept.

Referring to FIGS. 9, 12A, and 12B, each of the first to fourth measurement sensors 2501 to 2504 may include a first-type measurement sensor 2500_1 or a second-type measurement sensor 2500_2.

The first-type measurement sensor 2500_1 may include a light emitter 250R1 and a light receiver 250P1. The light emitter 250R1 may be a red light source for emitting red light, and the light receiver 250P1 may be a photodiode.

The second-type measurement sensor 2500_2 may include a light emitter 25011 and a light receiver 250P2. The light emitter 25011 may be an infrared light source for emitting infrared light, and the light receiver 250P2 may be a photodiode.

Figure 13:
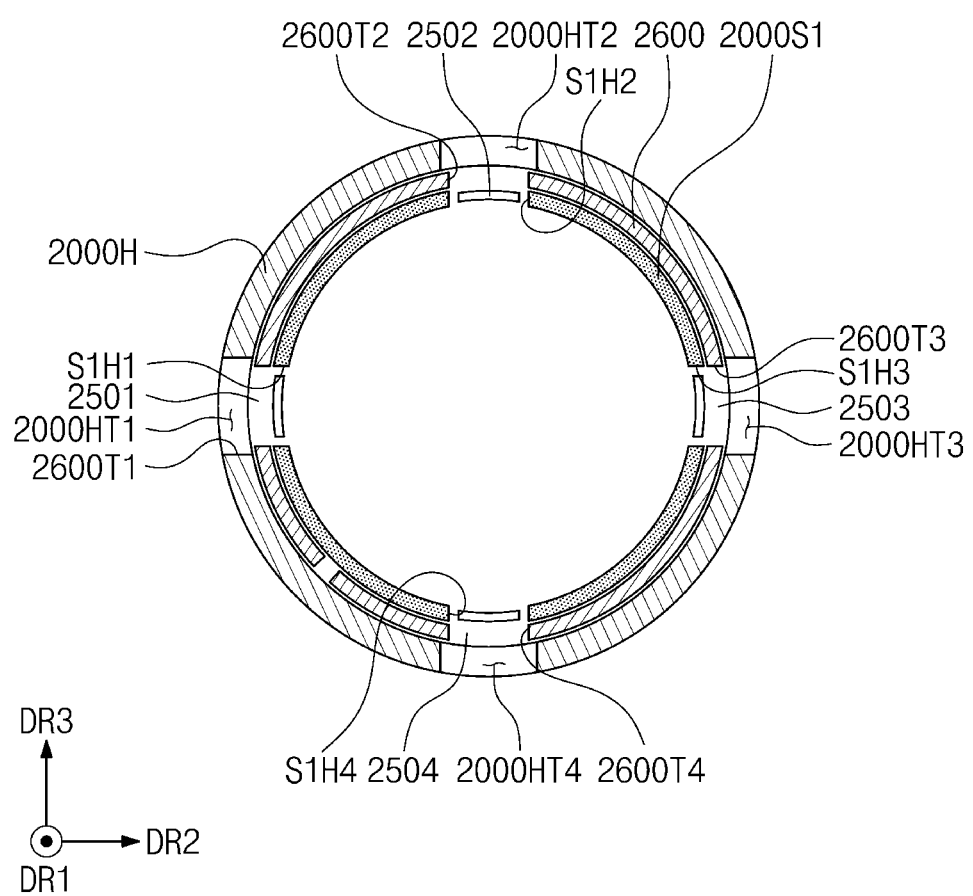
FIG. 13 is a cross-sectional view of an input device according to some embodiments of the inventive concept.

FIG. 13 is a cross-sectional view of an input device according to some embodiments of the inventive concept.

Compared to the embodiments described with respect to FIG. 9, the embodiments described with respect to FIG. 13 may be different with respect to a support part 2000S1. First to fourth support openings S1H1 to S1H4 may be defined in the support part 2000S1.

The first to fourth support openings S1H1 to S1H4 may face the first to fourth transmissive portions 2000HT1 to 2000HT4 respectively. The first to fourth support openings S1H1 to S1H4 may face the first to fourth openings 2600T1 to 2600T4 respectively.

The first to fourth measurement sensors 2501 to 2504, the first to fourth support openings S1H1 to S1H4, the first to fourth openings 2600T1 to 2600T4, and the first to fourth transmissive portions 2000HT1 to 2000HT4 may overlap corresponding components.

Figure 14:
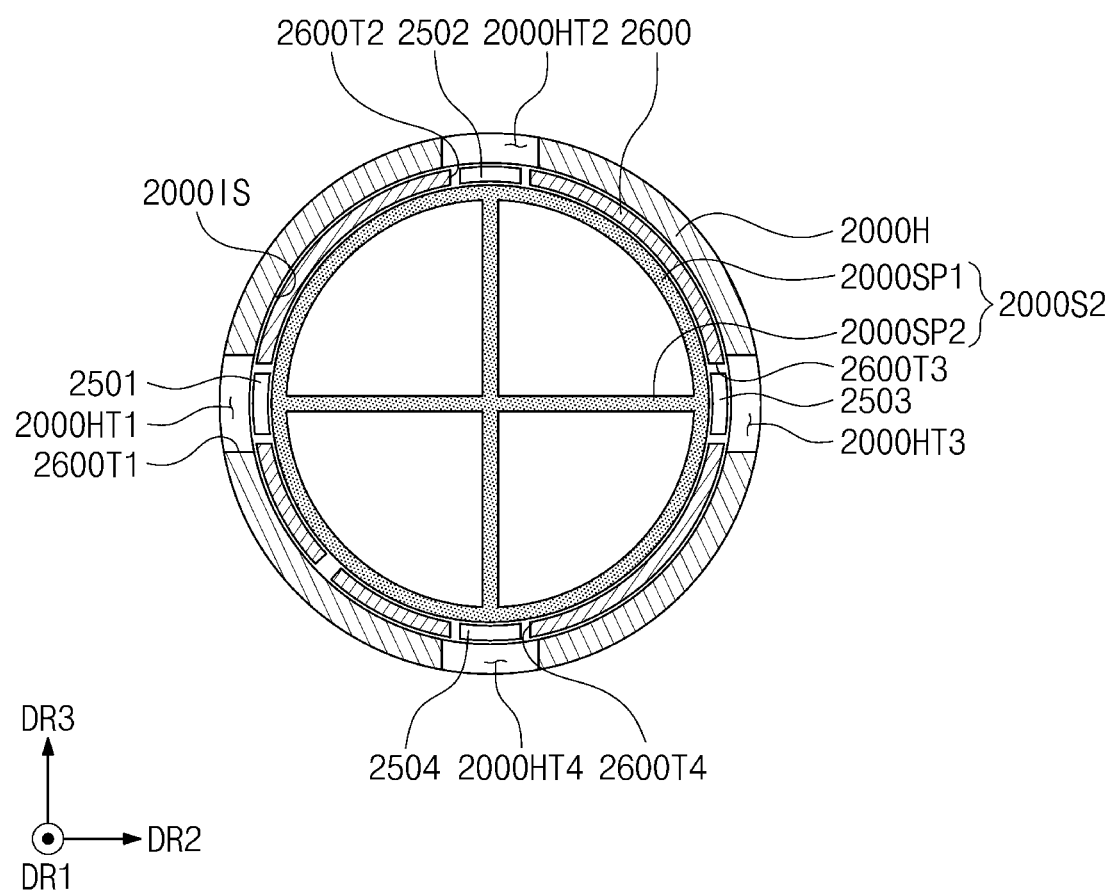
FIG. 14 is a cross-sectional view of an input device according to some embodiments of the inventive concept.

FIG. 14 is a cross-sectional view of an input device according to some embodiments of the inventive concept.

Compared to the embodiments described with respect to FIG. 9, the embodiments illustrated in FIG. 14 is different with respect to a support part 2000S2. The support part 2000S2 may include a first portion 2000SP1 and a second portion 2000SP2.

The first portion 2000SP1 may have a shape conforming to the inner circumferential surface 2000IS of the housing 2000H. The second portion 2000SP2 may be surrounded by the first portion 2000SP1, and may serve to reinforce the first portion 2000SP1. FIG. 14 illustrates an example in which the second portion 2000SP2 has a cross shape in a cross-section view, but the shape of the second portion 2000SP2 is not limited thereto.

Figure 15:
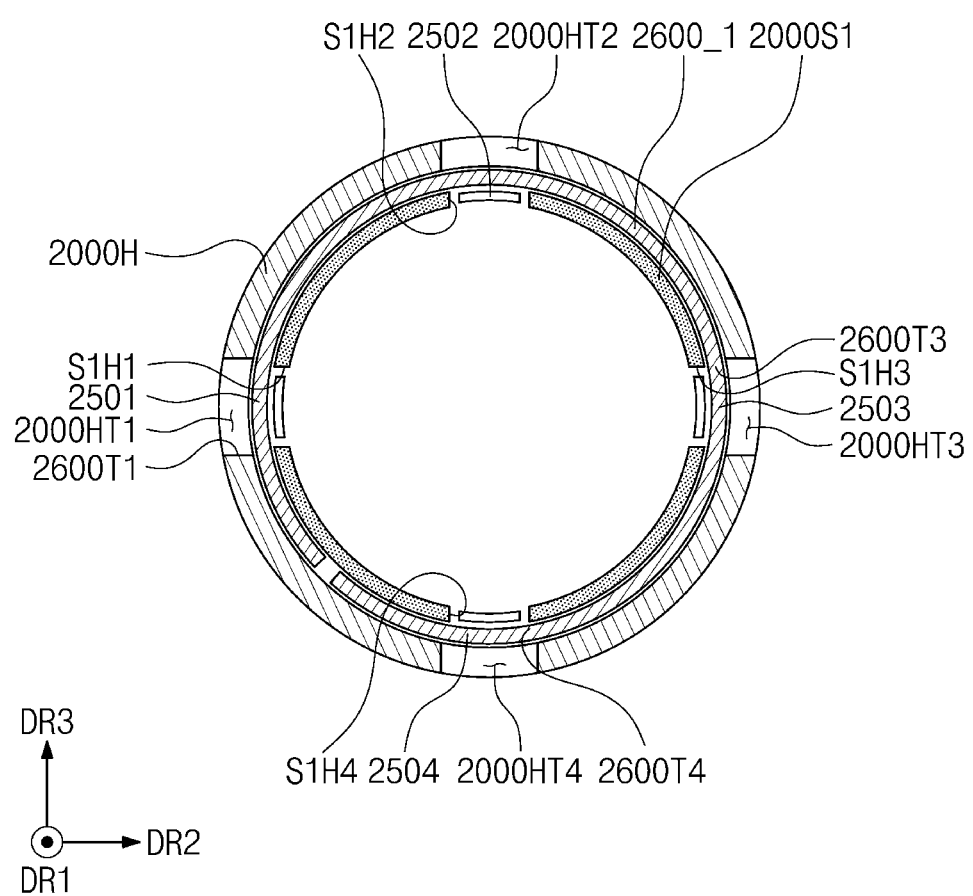
FIG. 15 is a cross-sectional view of an input device according to some embodiments of the inventive concept.

FIG. 15 is a cross-sectional view of an input device according to some embodiments of the inventive concept.

Compared to the embodiments described with respect to FIG. 13, the embodiments described with respect to FIG. 15 are different with respect to a pressure sensor 2600_1.

Referring to FIG. 15, the pressure sensor 2600_1 may be transparent. In this case, an opening may not be provided to the pressure sensor 2600_1. The first to fourth measurement sensors 2501 to 2504 may face the first to fourth transmissive portions 2000HT1 to 2000HT4 respectively.

Light provided from the measurement sensor 2500 and light reflected from the user may be transmitted through the first to fourth transmissive portions 2000HT1 to 2000HT4 and the transparent pressure sensor 2600_1.

However, embodiments according to the inventive concept are not limited thereto, and, thus, openings may be provided in correspondence with the first to fourth transmissive portions 2000HT1 to 2000HT4 even if the pressure sensor 2600_1 is transparent.

Figure 16:
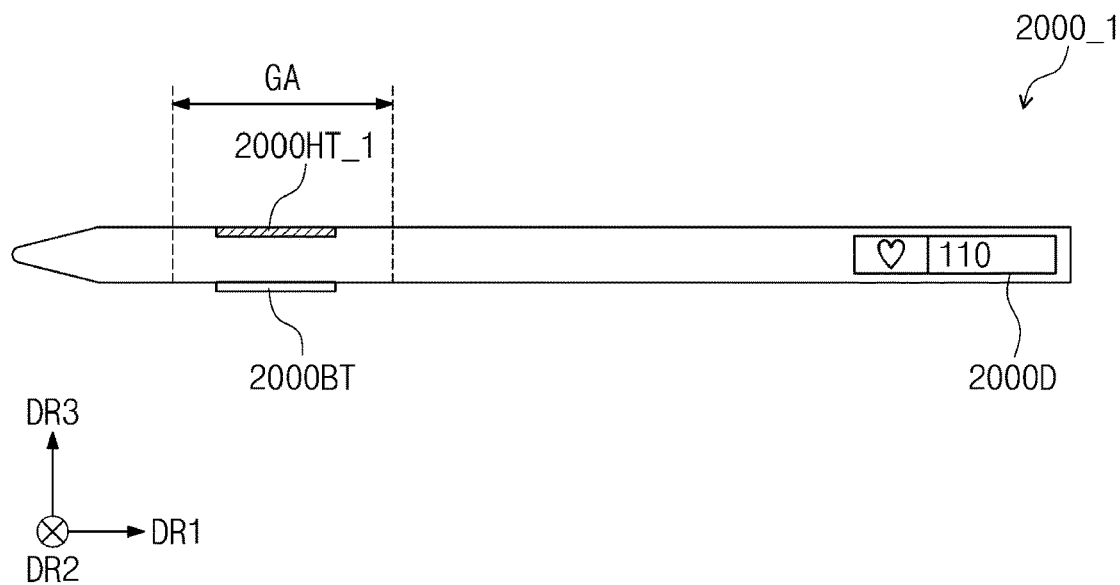
FIG. 16 is a diagram illustrating an input device according to some embodiments of the inventive concept.
Figure 17:
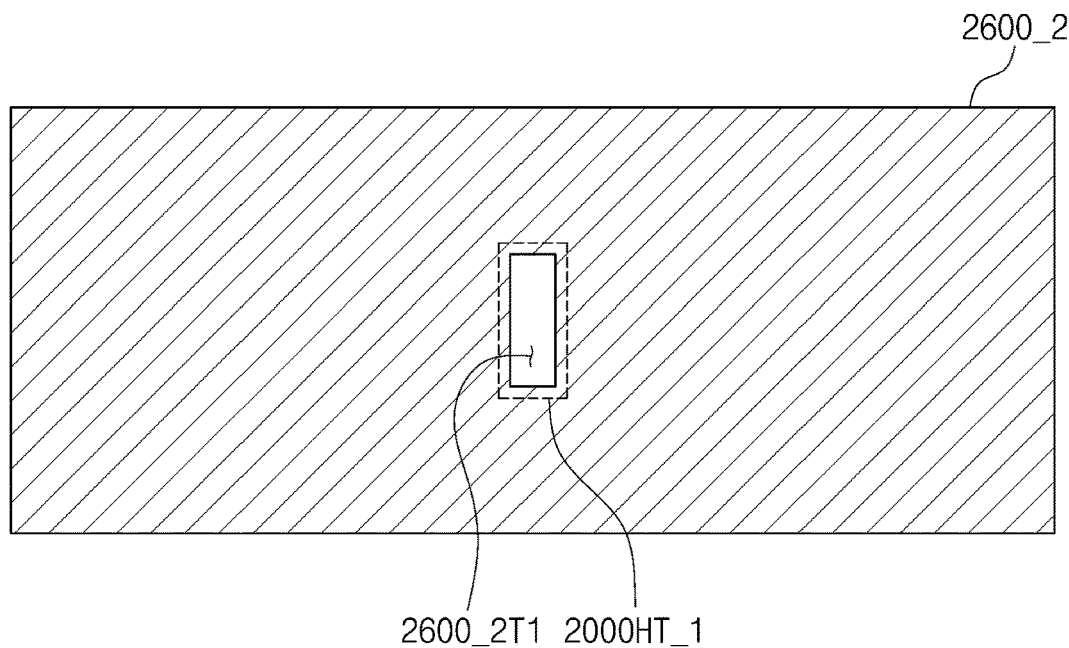
FIG. 17 is a planar view illustrating a pressure sensor according to some embodiments of the inventive concept.

FIG. 16 is a diagram illustrating an input device according to some embodiments of the inventive concept. FIG. 17 is a planar view illustrating a pressure sensor according to some embodiments of the inventive concept.

Compared to the input device 2000 illustrated in FIG. 8, the input device 2000_1 illustrated in FIG. 16 may further include an operation portion 2000BT and a display 2000D.

Referring to FIGS. 16 and 17, a transmissive portion 2000HT_1 may be defined in the holding portion GA of the input device 2000_1. The transmissive portion 2000HT_1 may be a region through which light provided from the measurement sensor 2500 (see FIG. 7) and light reflected from the user are transmitted. An opening 2600_2T1 may be defined in a region corresponding to the transmissive portion 2000HT_1 in a pressure sensor 2600_2.

The operation portion 2000BT may be located in a region facing the transmissive portion 2000HT_1. The operation portion 2000BT may include a pressing button or a touch button, but is not particularly limited thereto.

The display 2000D may display information obtained from the measurement sensor 2500 (see FIG. 7) and the pressure sensor 2600_2. Therefore, the user may check, in real time, biometric information about the user through the display 2000D while using the input device 2000_1.

As described above, an input device may include a pressure sensor and measurement sensor for measuring the blood pressure of a user. Therefore, while the user is performing a task using the input device, the blood pressure of the user may be measured periodically or aperiodically without additional equipment such as a cuff.

Although aspects of some embodiments according to the present invention have been described, it is understood that the present invention should not be limited to these example embodiments but various changes and modifications can be made by one ordinary skilled in the art within the spirit and scope of the present invention according to the following claims and their equivalents.

What is claimed is:

1. An input device comprising:
   a housing having a transmissive portion;
   a communicator in the housing and configured to exchange a signal externally;
   a pressure sensor configured to detect a value of a pressure applied on an external circumferential surface of the housing toward an interior of the housing and disposed in the housing along an inner circumferential surface of the housing and curved along the inner circumferential surface of the housing; and a measurement sensor in the housing and facing the transmissive portion to transmit or receive light through the transmissive portion, wherein a portion of the pressure sensor facing the transmissive portion has an opening.

2. The input device of claim 1, wherein a portion of the housing facing the pressure sensor includes rubber or plastic.

3. The input device of claim 1, further comprising a support part spaced apart from the inner circumferential surface of the housing with the pressure sensor therebetween.

4. The input device of claim 3, wherein the support part comprises a first portion having a shape conforming to a shape of the inner circumferential surface of the housing and a second portion surrounded by the first portion and reinforcing the first portion.

5. The input device of claim 1, wherein the pressure sensor is a film-type pressure sensor and is flexible.

6. The input device of claim 1, wherein the pressure sensor is transparent.

7. The input device of claim 1, wherein the measurement sensor comprises a light emitter configured to provide light and a light receiver configured to detected reflected light.

8. The input device of claim 7, wherein the light emitter comprises at least one of an infrared light source for emitting infrared light or a red light source for emitting red light, and the light receiver is a photodiode.

9. The input device of claim 1, wherein the measurement sensor is a photoplethysmography sensor, and is configured to measure at least one of a blood pressure, oxygen saturation, or heart rate of a user.

10. The input device of claim 1, further comprising a display configured to display information obtained from the pressure sensor and the measurement sensor.

11. The input device of claim 1, wherein the input device is an active pen, and the communicator is configured to receive an uplink signal from an external source and to output a downlink signal.

12. An interface device comprising:
a display device comprising a display layer and a sensor layer on the display layer; and
an input device configured to receive an uplink signal from the sensor layer and to output a downlink signal to the sensor layer,
wherein the input device comprises a housing, a measurement sensor and a pressure sensor, and
wherein the pressure sensor is configured to detect a value of a pressure applied on an external circumferential surface of the housing toward an interior of the housing to measure a blood pressure of a user and is disposed in the housing along an inner circumferential surface of the housing and is curved along the inner circumferential surface of the housing,
wherein the housing has a transmissive portion facing the measurement sensor, and
wherein an opening is defined in a portion of the pressure sensor facing the transmissive portion.

13. The interface device of claim 12, wherein the input device further comprises:
a support part in the housing;
a communicator in the housing and configured to receive the uplink signal and to transmit the downlink signal; and
an electrode electrically connected to the communicator,
wherein the pressure sensor and the measurement sensor are in the housing.

14. The interface device of claim 13, wherein the measurement sensor faces the transmissive portion, and the measurement sensor transmits or receives light through the transmissive portion.

15. The interface device of claim 13, wherein an opening is defined in a portion of the pressure sensor facing the transmissive portion.

16. The interface device of claim 13, wherein the pressure sensor is between the housing and the support part, and the support part comprises a first portion having a shape conforming to a shape of the inner circumferential surface of the housing and a second portion surrounded by the first portion and reinforcing the first portion.

17. The interface device of claim 13, wherein a portion of the housing facing the pressure sensor includes rubber or plastic.

18. The interface device of claim 12, wherein the measurement sensor comprises a light emitter configured to provide light and a light receiver configured to detect reflected light, wherein the light emitter comprises at least one of an infrared light source for emitting infrared light or a red light source for emitting red light, and the light receiver is a photodiode.

19. The interface device of claim 12, wherein the pressure sensor is a film-type pressure sensor and is flexible.

\* \* \* \* \*